(12) United States Patent
Golden et al.

(10) Patent No.: US 12,419,504 B2
(45) Date of Patent: *Sep. 23, 2025

(54) BRAKING MECHANISMS FOR STEERABLE MEDICAL DEVICES AND RELATED METHODS

(71) Applicant: Boston Scientific Scimed, Inc., Maple Grove, MN (US)

(72) Inventors: John B. Golden, Norton, MA (US); Evan Wilder, Boston, MA (US); Colby Harris, Weston, MA (US); Michael McBrien, Jamaica Plain, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/640,073

(22) Filed: Apr. 19, 2024

(65) Prior Publication Data

US 2024/0260819 A1    Aug. 8, 2024

Related U.S. Application Data

(63) Continuation of application No. 17/880,416, filed on Aug. 3, 2022, now Pat. No. 11,986,157.

(Continued)

(51) Int. Cl.
*A61B 1/005* (2006.01)
*G05G 1/01* (2008.04)

(52) U.S. Cl.
CPC ............. *A61B 1/0052* (2013.01); *G05G 1/01* (2013.01)

(58) Field of Classification Search
CPC .......... G05G 1/02; A61B 1/0052; F16D 41/18
See application file for complete search history.

(56) References Cited

U.S. PATENT DOCUMENTS

| 5,014,685 A | 5/1991 | Takahashi |
| 8,808,168 B2 | 8/2014 | Ettwein et al. |

(Continued)

FOREIGN PATENT DOCUMENTS

| DE | 102007026597 A1 | 12/2007 |
| FR | 2720895 A1 | 12/1995 |
| JP | 2002034901 A | 2/2002 |

OTHER PUBLICATIONS

International Search Report and Written Opinion issued in International Application No. PCT/US2022/039307, issued Nov. 11, 2022 (27 pages).

*Primary Examiner* — Daniel D Yabut
(74) *Attorney, Agent, or Firm* — Bookoff McAndrews PLLC

(57) ABSTRACT

A steering system for a medical device may include a first drive member having a central longitudinal axis; a central shaft extending through the first drive member; a control knob coupled to the first drive member; a braking knob coupled to the central shaft and including a first protrusion; and a brake shoe member coupled to the central shaft between the control knob and the braking knob. The first protrusion may be positioned within a first channel of the brake shoe member; the first protrusion may be configured to engage the brake shoe member to move a first arm of the brake shoe member radially outward towards a wall of the control knob when the braking knob is rotated in a first direction; and the first arm may be configured to move away from the wall when the braking knob is rotated in a second direction.

20 Claims, 6 Drawing Sheets

Related U.S. Application Data

(60) Provisional application No. 63/203,902, filed on Aug. 4, 2021.

(56) References Cited

U.S. PATENT DOCUMENTS

| | | |
|---|---|---|
| 2009/0287188 A1 | 11/2009 | Golden et al. |
| 2011/0088498 A1 | 4/2011 | Ettwein et al. |
| 2012/0277535 A1 | 11/2012 | Hoshino |
| 2015/0364271 A1 | 12/2015 | Huang |
| 2016/0000304 A1 | 1/2016 | Golden et al. |

BRAKING MECHANISMS FOR STEERABLE MEDICAL DEVICES AND RELATED METHODS

CROSS REFERENCE TO RELATED APPLICATION

This application is a continuation of U.S. patent application Ser. No. 17/880,416, filed on Aug. 3, 2022, which claims priority to U.S. Provisional Application No. 63/203,902, filed Aug. 4, 2021, each of the entirety of which is incorporated herein by reference.

TECHNICAL FIELD

This disclosure generally relates to medical systems, devices, and related methods that may be used to treat a subject. Aspects of the disclosure relate to medical devices and related methods for endoscopic or other medical procedures that incorporate a steerable medical device, among other aspects.

BACKGROUND

Current medical devices, such as catheters and endoscopes, are employed for examination and/or treatment of the mammalian body. In particular, various surgical procedures employ a catheter, endoscope, or other device to exam remote parts of the body and/or introduce surgical tools, fluids or other materials into the body for treatment thereof. For example, in some procedures, catheters and endoscopes may be used for the introduction of items, including but not limited to radiographic contrast materials, drugs, angioplasty balloons, stents, fiber optic scopes, laser lights, and cutting instruments (e.g. biopsy forceps, RF cutters, atherectomy devices, etc.), into vessels, cavities, passageways, or tissues of the body.

It is known in the pertinent art to provide the steerable catheter or endoscope with a braking mechanism for arresting the relative deflection of the elongated shaft during use. In a conventional manner, the control knobs are manually operated to articulate the elongated shaft for navigation through a vessel, cavity, or passageway of a patient. Manual release of the control knobs returns the elongated shaft to its straight condition. At certain points during any particular surgical procedure, it may be desired to arrest the relative orientation of the elongated shaft. At such time, the conventional braking mechanism is activated and movement of both control knobs relative to the remainder of the catheter is simultaneously precluded.

While known braking mechanisms for steerable catheters and endoscopes have proven to be acceptable for their intended applications, they are associated with limitations. For example, a user may experience increased fatigue due to the amount of force required to activate a braking mechanism using one or more control knobs. Furthermore, often braking mechanisms for steerable catheters and endoscopes include an excessive amount of internal components, which increases cost of production and increases production time for assembly of the system.

These concerns may increase the duration, costs, and risks of medical procedures that require steerable catheters and/or endoscopes. The systems, devices, and methods of this disclosure may rectify some of the deficiencies described above or address other aspects of the art.

SUMMARY

Examples of the disclosure relate to, among other things, systems, devices, and methods for performing one or more medical procedures with the medical systems and devices. Each of the examples disclosed herein may include one or more of the features described in connection with any of the other disclosed examples.

In some aspects, a steering system for a medical device may include a first drive member having a central longitudinal axis; a central shaft extending through the first drive member; a control knob coupled to the first drive member; a braking knob coupled to the central shaft and including a first protrusion; and a brake shoe member coupled to the central shaft between the control knob and the braking knob. The first protrusion may be positioned within a first channel of the brake shoe member; the first protrusion may be configured to engage the brake shoe member to move a first arm of the brake shoe member radially outward, relative to the central longitudinal axis, towards a wall of the control knob when the braking knob is rotated in a first direction; and the first arm may be configured to move away from the wall of the control knob when the braking knob is rotated in a second direction opposite the first direction.

In other aspects, the steering system may include one or more of the following features. A dual-stop member coupled to the central shaft and positioned between the brake shoe member and the control knob. The dual-stop member may be configured to limit rotation of the control knob and the braking knob. The dual-stop member may be coupled to the brake shoe member via at least one pin. The braking knob may further include a second protrusion, the brake shoe member may include a second arm and a second channel, and the second protrusion may be positioned within the second channel, and may be configured to engage the brake shoe member to move the second arm radially outward, relative to the central longitudinal axis, towards the wall of the control knob when the braking knob is rotated in the first direction. The control knob may include a recess, and the recess may receive the brake shoe member and the first protrusion. The brake shoe may include a central portion including a lumen configured to receive the central shaft; a first protrusion extending radially-outward, relative to the central longitudinal axis, from the central portion; a second protrusion extending radially-outward, relative to the central longitudinal axis, from the central portion; the first arm extending outward from the first protrusion, and the first arm may be curved towards the central shaft and include a first expanded end and a first recess; and a second arm extending outward from the second protrusion, and the second arm may be curved towards the central shaft and include a second expanded end and a second recess.

In other aspects, the steering system may include one or more of the following features. The braking knob may include a second protrusion, and the first recess may be configured to receive the first protrusion and the second recess may be configured to receive the second protrusion. The first expanded end may include a rough surface, grooves, and/or teeth configured to engage the wall; and the second expanded end may include a rough surface, grooves, and/or teeth configured to engage the wall. The brake shoe may further include: a first spring beam extending from the first arm and extending at least partially within the first recess; and a second spring beam extending from the second arm and extending at least partially within the second recess. The brake shoe may further include: a first lumen extending through the first expanded end; and a second lumen extending through the second expanded end. The first recess may extend from the first expanded end to a portion of the first arm spaced from the expanded end. The brake shoe member may include: a central portion including a lumen configured to receive the central shaft; a first protrusion extending radially-outward, relative to the central longitudinal axis, from the central portion; a second protrusion extending radially-outward, relative to the central longitudinal axis, from the central portion; the first arm extending outward from the first protrusion, wherein the first arm is curved towards the central shaft and includes a first end, a first expanded portion positioned between the first end and the first protrusion, and a first recess proximate to the first end; and a second arm extending outward from the second protrusion, wherein the second arm is curved towards the central shaft and includes a second end, a second expanded portion positioned between the second end and the second protrusion, and a second recess proximate to the second end. The first protrusion may be spaced from the central shaft. The first arm may extend circumferentially around the central longitudinal axis.

In other aspects, a steering system for a medical device may include: a handle housing configured for connection to a deflectable insertion shaft; a first drive member; a control knob coupled to the first drive member; and a braking mechanism configured to lock the first drive member. The braking mechanism may include: a central shaft extending through the first drive member, coupled to the handle housing, and having a central longitudinal axis; a braking knob coupled to the central shaft and including a first protrusion; and a brake shoe member, wherein the first protrusion is positioned within a first channel of the brake shoe member; wherein a first arm of the brake shoe member is configured to move radially outward, relative to the central longitudinal axis, towards a wall of the control knob when the braking knob is rotated in a first direction. In some examples, the first protrusion may be configured to engage the brake shoe member to move the first arm of the brake shoe member radially outward, relative to the central longitudinal axis, towards a wall of the control knob when the braking knob is rotated in the first direction; and the first protrusion may be configured to be positioned within a first recess of the first arm when the braking mechanism is in a fully locked position. The wall may face radially-inward towards the central longitudinal axis. The braking mechanism may further comprise a dual-stop member configured to limit rotation of the control knob and the braking knob.

In other aspects, a steering system for a medical device may include: a first drive member coupled to the first steering wire and having a central longitudinal axis; a control knob coupled to the first drive member; a braking knob coupled to a central shaft and including a first protrusion; and a brake shoe member coupled to the central shaft between the control knob and the braking knob, wherein the first protrusion is positioned within a first channel of the brake shoe member, and wherein the brake shoe member is configured to apply a frictional force to a radially-inward facing, relative to the central longitudinal axis, wall of the control knob.

It may be understood that both the foregoing general description and the following detailed description are exemplary and explanatory only and are not restrictive of this disclosure, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Figure 1:
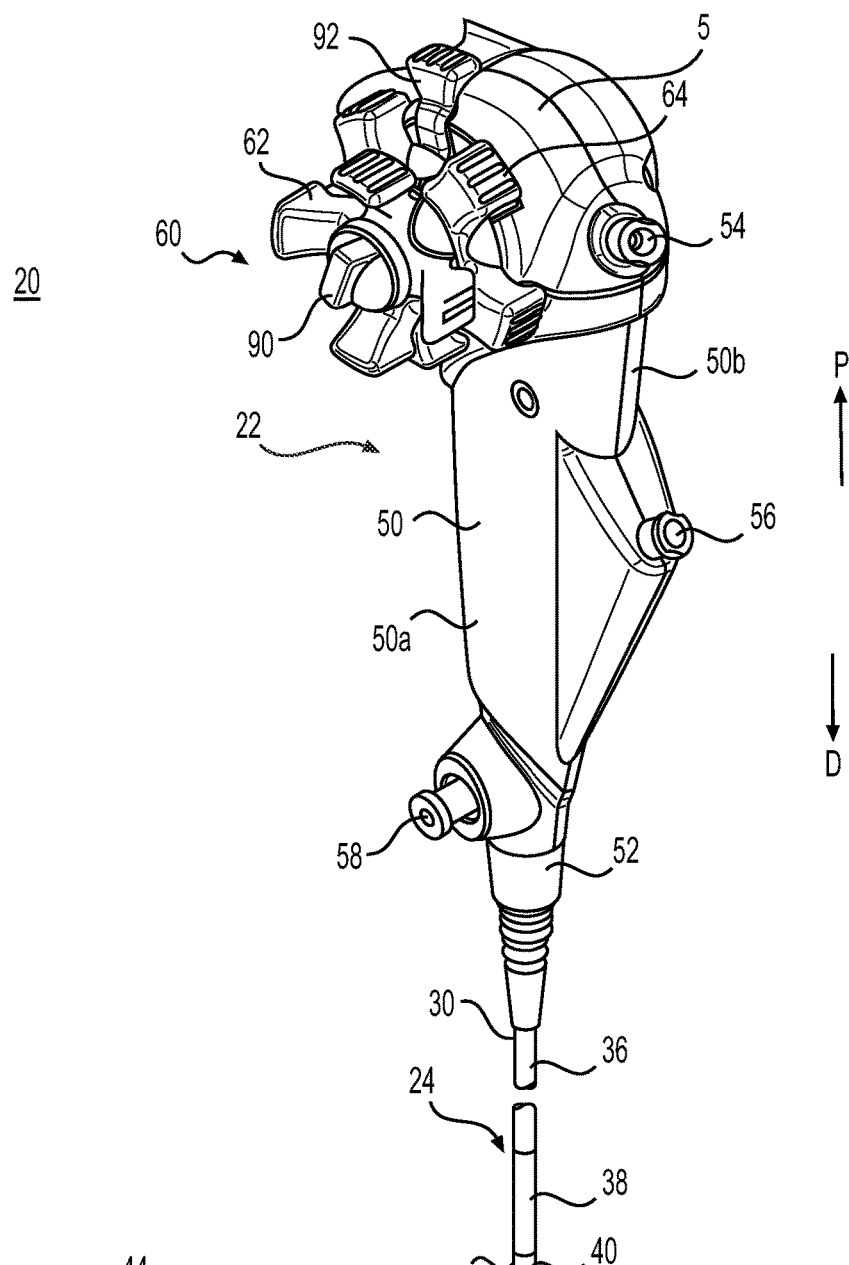
FIG. 1 illustrates a perspective view of a steerable medical device, according to aspects of this disclosure.

The terms "proximal" and "distal" are used herein to refer to the relative positions of the components of an exemplary medical system and exemplary medical devices. When used herein, "proximal" refers to a position relatively closer to the exterior of the body of a subject or closer to a medical professional using the medical system or medical device. In contrast, "distal" refers to a position relatively further away from the medical professional using the medical system or medical device, or closer to the interior of the body of the subject. Proximal and distal directions are labeled with arrows marked "P" and "D", respectively, throughout the figures. As used herein, the terms "comprises," "comprising," "having," "including," or other variations thereof, are intended to cover a non-exclusive inclusion, such that a system, device, or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Embodiments of this disclosure are generally directed to steerable devices of the type having a control handle and a deflectable insertion shaft that is inserted into a conduit, passageway, body lumen, etc. Several embodiments of this disclosure are generally directed to steering systems employed by the steerable devices for controlling the deflection of the insertion shaft, and in particular, to steering systems that comprise a braking mechanism for locking the distal end of the insertion shaft at a desired deflection angle. Embodiments of this disclosure may also be directed to control handles, medical devices, or methods using such medical devices that employ such steering systems.

Navigation of the catheter, endoscope, or other device through the vessels, cavities, or passageways of the body to the area of interest is critical to the success of the examination and/or treatment. To this end, modern catheters and endoscopes include an arrangement that allows the operator to deflect the distal end of an associated insertion shaft for guiding the insertion shaft through the passageways, vessels, etc., to the area of interest. For example, conventional steerable catheters and endoscopes typically comprise a control handle from which an elongated insertion shaft extends. The elongated insertion shaft is formed of a material or materials of such stiffness so as to normally maintain the elongated shaft in a straight condition in the absence of an external force. The outer end portion of the elongated shaft is relatively flexible to permit deflection. Pairs of steering wires are connected to the control handle, extend outwardly through the elongated shaft, and terminate at the flexible outer end portion of the elongated shaft. A steering wire control mechanism is carried by the control handle and includes a pair of rotatable control knobs that cooperate with the respective pairs of steering wires for manually controlling the bending of the flexible outer end portion of the elongated tube to thereby effectively "steer" the catheter or endoscope in the up/down and right/left directions.

Although exemplary embodiments of this disclosure will be described with reference to a steerable catheter, it will be appreciated that aspects of this disclosure have wide application, and thus may be suitable for use with many types of medical devices, such as endoscopes (e.g. bronchoscopes, colonoscopes, gastroscopes, duodenoscopes, etc.), steerable fiberscopes, steerable guidewires, etc., and non-medical devices, such as borescopes. Accordingly, the following descriptions and illustrations should be considered illustrative in nature, and thus, not limiting the scope of this disclosure.

FIG. 1 illustrates an exemplary steerable device 20 including a control handle 22 and an insertion shaft 24 extending outwardly therefrom. In use, the insertion shaft 24 may be navigated through vessels, cavities, passageways, or tissues of a mammalian body to an area of interest for examination and/or treatment thereof. In some examples, insertion shaft 24 may enter a body through an orifice, for example, the nose, mouth, or anus, and the placement of the insertion shaft 24 can be in any portion of the GI tract, including the esophagus, stomach, duodenum, large intestine, or small intestine. Steerable device 20 may be capable of introducing items, including but not limited to radiographic contrast materials, drugs, angioplasty balloons, stents, fiber optic scopes, laser lights, cutting instruments (e.g., biopsy forceps, radio frequency cutters, atherectomy devices, etc.), and other endoscopic and medical devices (e.g., aspiration and infusion catheters, stone baskets, needles, cytology brushes, snares, ablation devices, etc.) to the area of interest.

As will be discussed in further detail below, steerable device 20 includes a steering system that controls the deflection angle of the distal end of the insertion shaft 24 in two or more non-planar directions for navigating the insertion shaft 24 through the body lumens, passageways, etc., to the area of interest. As will be further described in detail below, embodiments of the steering system may also include an exemplary braking or locking mechanism for arresting the movement of the distal end of the insertion shaft 24 in a first direction independent of arresting movement of the distal end in a second non-planar direction.

Insertion shaft 24 may be formed as an elongated body having a proximal end 30 and a distal end 32. The insertion shaft 24 may be formed as a hollow tube, a multi-lumen extruded shaft as shown in the cross-sectional view of FIG. 2, or other structures that permit passage of a plurality of steering wires and optional instruments, such as biopsy forceps, visions probes, cutters, snares, etc., to the distal end 32. In one example, insertion shaft 24 is cylindrical and may be constructed using various techniques known in the art from any suitable material, such as PEBA® (polyether block amides), nylon, polytetrafluroethylene (PTFE), polyethylene, polyurethane, fluorinated ethylene propylene (FEP), thermoplastic polyurethane, thermoplastic elastomers, and the like, or combinations and blends thereof.

The insertion shaft 24 may be configured such that it is capable of being deflected or "steered" through or within the cavities, vessels, passageways, etc. of a body to an area of interest. To that end, the insertion shaft 24 may be constructed so that it varies in stiffness between the proximal end 30 and the distal end 32. In particular, the distal region of the insertion shaft 24 may be configured to be more flexible than the proximal region. This may allow the insertion shaft 24 to be easily advanced without compressing and with minimal twisting while providing deflection capabilities for deflecting the distal end 32. In some examples, the flexibility may be varied gradually (e.g. increasingly) throughout the length of the insertion shaft from its proximal end 30 to its distal end 32. In other examples, the distal region of the insertion shaft (e.g., the most distal 1-4 inches of the insertion shaft) may be made more flexible (i.e. less stiff) than the remainder of the insertion shaft.

As shown in FIG. 1, insertion shaft 24 may be comprised of a proximal section 36, a more flexible deflection section 38 positioned distally of the proximal section 36, and a distal tip 40 located at the distal end 32. Deflectable section 38 may be constructed of a material with less stiffness than the proximal section 36. In other examples, deflection section 38 may be an articulating joint or series of articulation joints. For example, the deflection section 38 may include a plurality of segments that allow the distal end to deflect in two or more non-planar directions.

Figure 2:
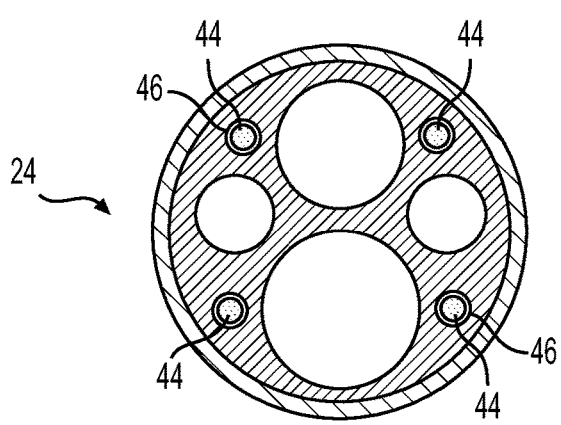
FIG. 2 illustrates a cross-sectional view of the insertion shaft of the steerable medical device of FIG. 1, according to aspects of this disclosure.

Steerable device 20 may further include a plurality of steering wires 44 that may cause the distal end 32 of the insertion shaft 24 (including deflection section 38 and tip 40) to deflect in two or more directions. As shown in FIG. 2, the steerable catheter may include two pairs of steering wires 44, each wire spaced approximately 90 degrees apart from adjacent wires, for providing four-way steering (i.e. up/down/left/right) of the insertion shaft 24. In other examples (not shown), the steerable catheter may include two steering wires 44 that may allow the user to steer the distal end in at least two directions. The steering wires 44 may be routed, for example, through a corresponding number of steering wire lumens of the insertion shaft 24. The lumens may be positioned within the wall of a tubular shaft, defined by tubes extending through a central bore of the tubular shaft, or defined by bores 46 of an extruded shaft as shown in FIG. 2. Steering wires 44 may have sufficient tensile strength and modulus of elasticity so that they do not deform (elongate) during curved deflection. In some examples, steering wires 44 may be made from stainless steel, may be lubricated, and/or may be housed in a PTFE thin-walled extrusion to help prevent the insertion shaft from binding up during deflection. Steering wires 44 may have any cross-sectional geometry, and are shown round in FIG. 2 as an exemplary embodiment.

The distal ends of the steering wires 44 may be secured at the distal end 32 of the insertion shaft 24 in any conventional manner such that tension applied to the steering wires 44 causes the distal end 32 to deflect in a controllable manner. In some examples, the steering wires 44 may be anchored to the distal tip of the insertion shaft 24 using conventional techniques, such as adhesive bonding, heat bonding, crimping, laser welding, resistance welding, soldering, etc. Steering wires 44 may extend from the distal end 32 of the insertion shaft 24 to the opposing proximal end 30 of the insertion shaft 24, and terminate in a suitable manner at a steering system carried by the control handle 22, as will be described in detail below.

Referring again to FIG. 1, the insertion shaft 24 is functionally connected at its proximal end 30 to the control handle 22. In the embodiment shown in FIG. 1, the control handle 22 includes a handle housing 50 formed by two housing halves 50a and 50b joined by appropriate removable fasteners, such as screws, or non-removable fasteners, such as rivets, snaps, heat bonding, adhesive bonding, or interference fits (e.g., crush pins etc.). Proximal end 30 of the insertion shaft 24 may be routed through a strain relief fitting 52 secured at the distal end of the handle housing 50. The handle housing 50 may include other features, if desired, such as one or more ports for providing access to optional channels of the insertion shaft 24. As shown in FIG. 1, handle housing 50 may include an imaging device port 54 (e.g. for connection to an umbilicus having imaging and/or lighting wiring), a working channel port 56, and an irrigation/suction port 58.

Handle housing 50 carries a steering system 60, which is constructed in accordance with aspects of this disclosure. In practice, an operator (e.g. physician, technician, etc.) manually operates steering system 60 for controlling the deflection of the distal end 32 of the insertion shaft 24 as the insertion shaft is advanced through passageways, body lumens, organs, etc., to an area of interest. In some examples, steering system 60 may include two movable members that are operatively connected to the distal end of the insertion shaft via steering wires 44. As shown in FIG. 1, the movable members are control knobs 62, 64, which are connected to two pairs of steering wires 44 for effecting four-way steering of the distal end 32 of the insertion shaft 24 in the up/down direction and in the right/left direction. For example, first control knob 62 may be connected to a pair of steering wires 44 to control up/down steering, and the second control knob 64 may be connected to a pair of steering wires 44 to control right/left steering. In other examples, other moveable members may be employed, such as steering dials, linear sliders, etc., for steering the distal end of the insertion shaft 24. In some examples, a single steering wire 44 may be coupled to each of the movable members, such as the first and second control knobs 62 and 64. In these examples, the termination locations of the wires may determine the directions in which the insertion shaft may deflect.

Steering system 60 may further include a braking mechanism that functions to lock or partially lock (e.g. inhibit further deflection of) the distal end of the insertion shaft 24 in a desired deflection position or angular position during use. For example, embodiments of the braking mechanism may be configured to lock the position of the distal end of the insertion shaft 24 in a first direction independently of movement of the distal end in a second direction. Stated differently, braking mechanisms described herein may be configured to arrest the movement of the distal end of the insertion shaft 24 in one direction while allowing the insertion shaft 24 to move in a second direction that is out of the plane of the first direction. This, in some examples, may be accomplished by arresting movement of the first and/or second control knobs 62 and 64, and/or arresting movement of the first and/or second pairs of steering wires 44 associated with the control knobs 62, 64. As shown in FIG. 1, actuation of braking knob 90 may be configured to arrest movement of control knob 62 and actuation of locking lever 92 may be configured to arrest movement of control knob 64. Although the braking mechanisms described herein below are discussed in relation to an outer control knob 62 and braking knob 90, any of the braking mechanisms discussed in this disclosure may be implemented using control knob 64 and/or locking lever 92.

Figure 3:
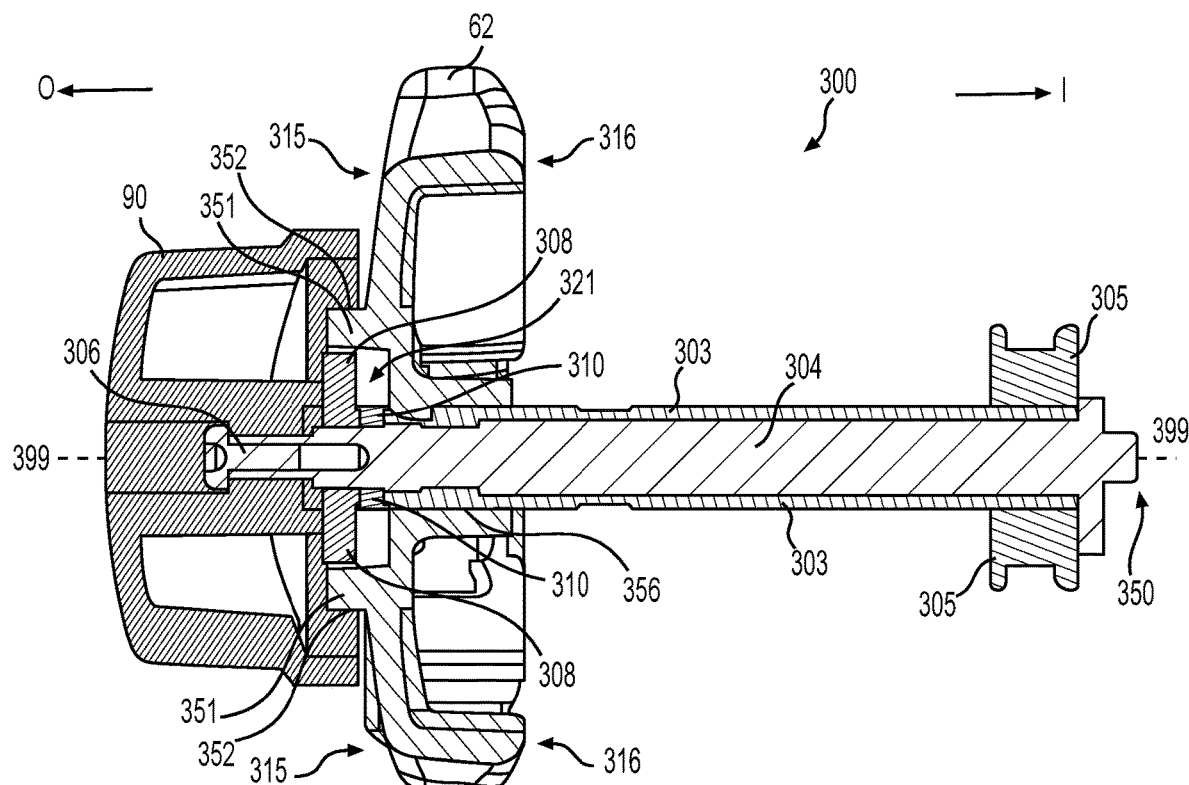
FIG. 3 illustrates a side, cross-sectional view of an exemplary braking mechanism, according to aspects of this disclosure.

FIG. 3 illustrates a side, cross-sectional view of a braking mechanism 300 including control knob 62 and braking knob 90. For purposes of explaining the construction of braking mechanism 300 in FIG. 3, an outward direction is shown by an arrow labeled "O" and an inward direction is shown by an arrow labeled "I". Control knob 62 may be coupled to drive member 303, and drive member 303 may be interconnected between control knob 62 and steering wires 44. The drive member (shaft) 303 is pressed onto the pulley assembly 305. Both the shaft 303 and pulley 305 rotate about the central shaft 304. The braking knob 90 is allowed to rotate approximately 80-120 degrees relative to the central shaft 304 as the locking mechanism is engaged or disengaged by the user. Brake shoe 308 and dual stop 310 are fixed relative to each other and the central shaft 304. Drive member 303 may be an integrally formed piece of material, such as plastic or metal, defining a tubular member extending from control knob 62 into handle 22 (not shown in FIG. 3). Pulley assembly 305 may be fixed to drive member 303 and coupled to steering wires 44 (not shown in FIG. 3). Rotation of drive member 303 about central longitudinal axis 399 may move steering wires 44 via pulley assembly 305. Accordingly, when a user rotates control knob 62 about axis 399, drive member 303 may move steering wires 44 to move deflectable section 38 of insertion shaft 24. A first end of drive member 303 may coupled to control knob 62 and a second end of drive member 303, at an opposite end from the first end, may be coupled to pulley assembly 305. Central shaft 304 may extend through drive member 303, and drive member 303 may rotate about central shaft 304. Central shaft 304 may be cylindrical and may be rotatably coupled to braking knob 90 such that braking knob 90 may rotate about central shaft 304 (about axis 399) without moving central shaft 304. In some examples, a screw 306 may couple braking knob 90 to central shaft 304. In some examples, an inward end 350 of central shaft 304 may be fixedly coupled to a portion of handle 22. Central shaft 304 may be fixedly coupled to brake shoe member 308 and dual-stop member 310, and may be configured to maintain the position of brake shoe member 308 and dual-stop member 310 relative to control knob 62 and braking knob 90.

Braking mechanism 300 may include brake shoe member 308 and dual-stop member 310. As shown in FIG. 3, brake shoe member 308 and dual-stop member 310 may be positioned between control knob 62 and braking knob 90, and may be fixedly coupled to central shaft 304. A recessed portion 321 of control knob 62 may receive brake shoe member 308 and dual-stop member 310, and recessed portion 321 may be facing the outward direction towards braking knob 90. A central lumen 356 may extend entirely through control knob 62, may be positioned at a central portion of recessed portion 308, and may be configured to receive drive member 303 and central shaft 304. A circular, outwardly-protruding portion 351 of control knob 62 may extend from a top surface 315 of control knob 62 and may extend around the circumference of recessed portion 321. The circular, outwardly-protruding portion 351 may be received by a circular recess 352 of braking knob 90. Braking knob 90 may be configured to rotate about axis 399 relative to control knob 62 and drive member 303. Control knob 62 and drive member 303 may be configured to rotate about axis 399 relative to central shaft 304, braking knob 90, brake shoe member 308, and dual-stop member 310. Central shaft 304 may extend through brake shoe member 308, dual-stop member 310, control knob 62, drive member 303, and pulley assembly 305; and may terminate at an inwardmost end of braking mechanism 300.

Figure 4:
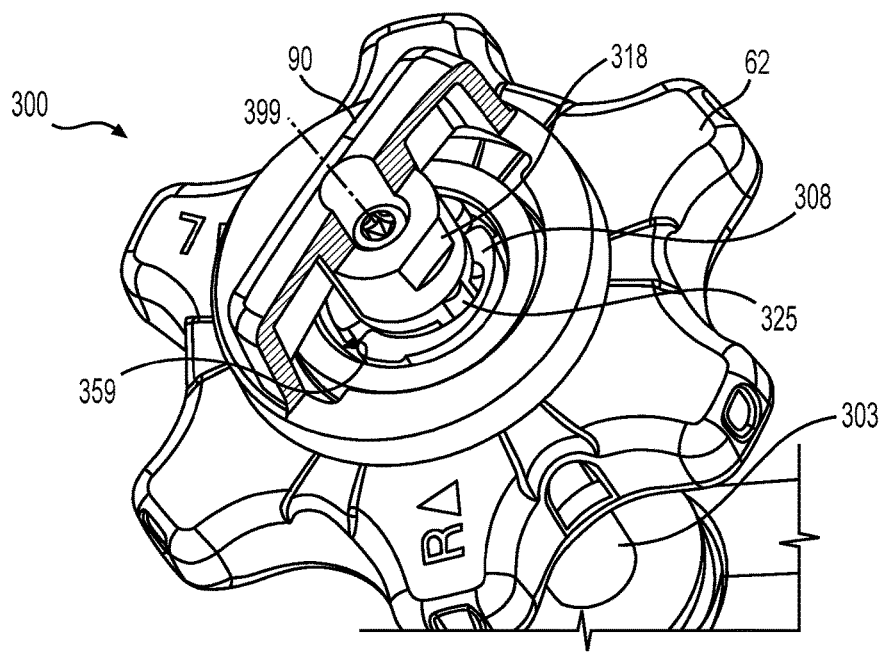
FIG. 4 illustrates a perspective, partial cross-sectional view of the exemplary braking mechanism of FIG. 3, according to aspects of this disclosure.

FIG. 4 illustrates a perspective view of the braking mechanism 300 shown in FIG. 3, with a portion of braking knob 90 shown in cross-section to expose brake shoe member 308 and a central portion 318 of braking knob 90. As shown in FIG. 4, central portion 318 of braking knob 90 may include a first protrusion 325, and a second protrusion 326 (shown in FIG. 7) on an opposite side of central portion 318, configured to engage with brake shoe member 308. First protrusion 325 and second protrusion 326 each protrudes radially outward from braking knob 90 towards brake shoe member 308. Central portion 318 may be cylindrical and may extend inward from an outward-most portion of braking knob 90. When positioned within recess 321 of control knob 62, each of first protrusion 325 and second protrusion 326 may abut brake shoe member 308. A radially-inward facing wall 359 forming a part of recess 321 of control knob 62 may be configured to engage with brake shoe member 308. As will be discussed in further detail herein below, first and second protrusions 325, 326 of braking knob 90 may, when braking knob 90 is rotated, push portions of brake shoe member 300 radially outward from axis 399 towards wall 359 of control knob 62 to push brake shoe member 308 against wall 359, and thus apply a braking force to control knob 62 to prevent rotation of control knob 62 about axis 399.

Figure 5:
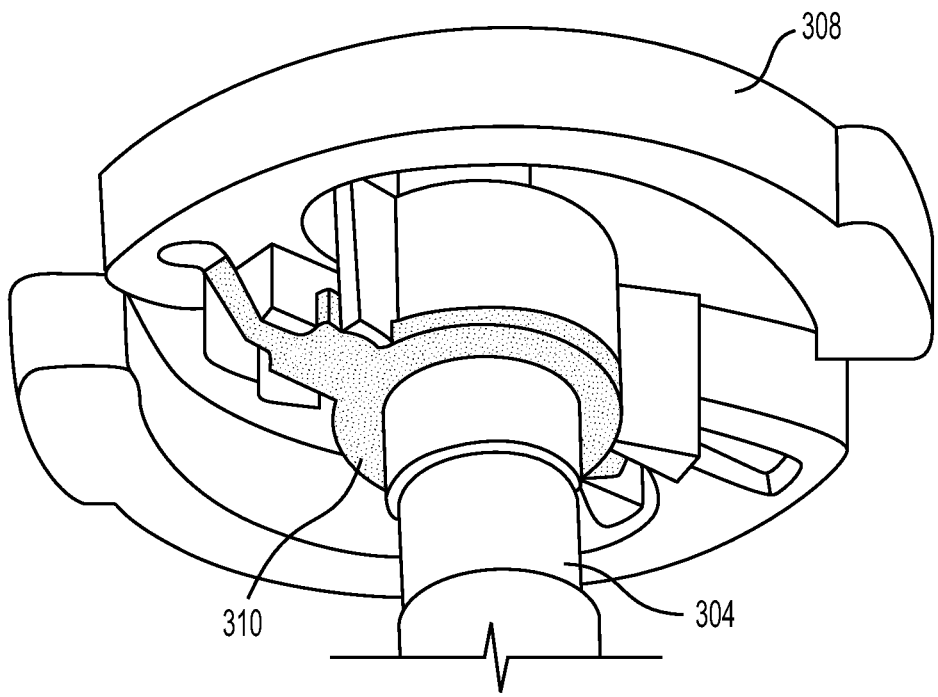
FIG. 5 illustrates a perspective view of exemplary components of the braking mechanism of FIG. 3, according to aspects of this disclosure.

FIG. 5 shows dual-stop member 310 positioned around central shaft 304 and received by brake shoe member 308. Dual-stop member 310 may be configured to abut against a portion of control knob 62 within recess 321. Each of dual-stop member 310 and brake shoe member 308 may be fixedly coupled to central shaft 304.

Figure 6:
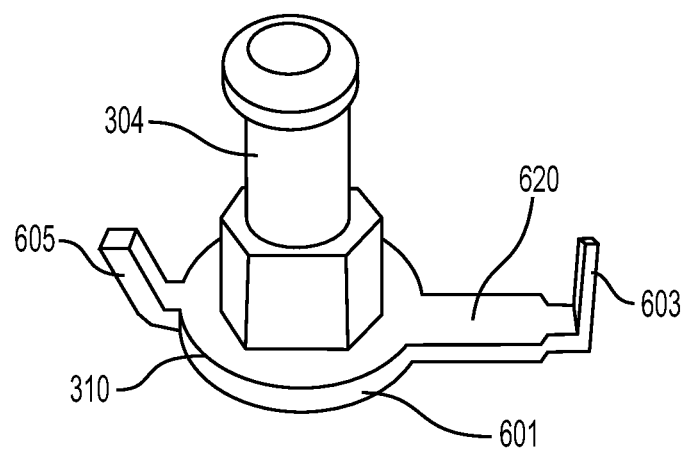
FIG. 6 illustrates a perspective view of exemplary components of the braking mechanism of FIG. 3, according to aspects of this disclosure.

FIG. 6 illustrates dual-stop member 310 positioned around central shaft 304, with a portion of central shaft 304 removed. Dual-stop member 310 may include a circular central portion 601, a rectangular protrusion 620 extending radially outward from central portion 601, and two tabs 603, 605 extending outward from, and transverse to, protrusion 620 and central portion 601, respectively. Each of tabs 603, 605 is configured to be received within a portion of brake shoe member 308, as may be seen in FIG. 5. As will be discussed further herein below, dual-stop member 310 may be configured to maintain the rotational position of brake shoe member 308 relative to control knob 62 and braking knob 90. Dual-stop member 310 may also increase the structural integrity of brake shoe member 308 and may help prevent brake shoe member 308 from breaking during operation of braking mechanism 300.

Figure 7:
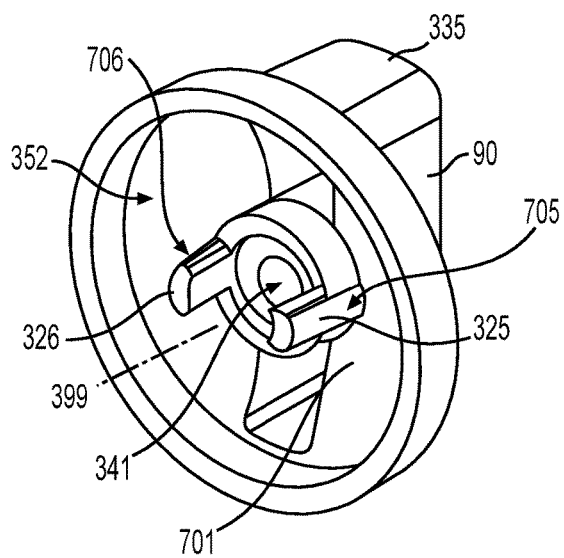
FIG. 7 illustrates a perspective view of an exemplary locking knob of the braking mechanism of FIG. 3, according to aspects of this disclosure.

FIG. 7 illustrates a perspective view of braking knob 90. Braking knob 90 may include a gripping portion 335 that may be rectangular shaped and configured for a user to grasp with one or more fingers and/or thumb. Braking knob 90 may include a central lumen 341 configured to receive central shaft 304, and central lumen 341 may be configured to fixedly couple braking knob 90 to central shaft 304 (e.g. via press-fit or an adhesive). Circular recess 352 may be positioned on an opposite side from gripping portion 90, and first protrusion 325 and second protrusion 326 may extend radially inward from an inward facing surface 701 of braking knob 90. First protrusion 325 may be positioned at an opposite side of central lumen 341 from second protrusion 326. First protrusion 325 and second protrusion 326 may be spaced from each other such that each of first protrusion 325 and second protrusion 326 may be received within channels 369, 370 (shown in FIG. 8) of brake shoe member 308. Each of first protrusion 325 and second protrusion 326 may have curved, radially-outward facing surfaces 705, 706, respectively, relative to axis 399. Each of surfaces 705, 706 may be configured to engage brake-shoe member 308.

Figure 8:
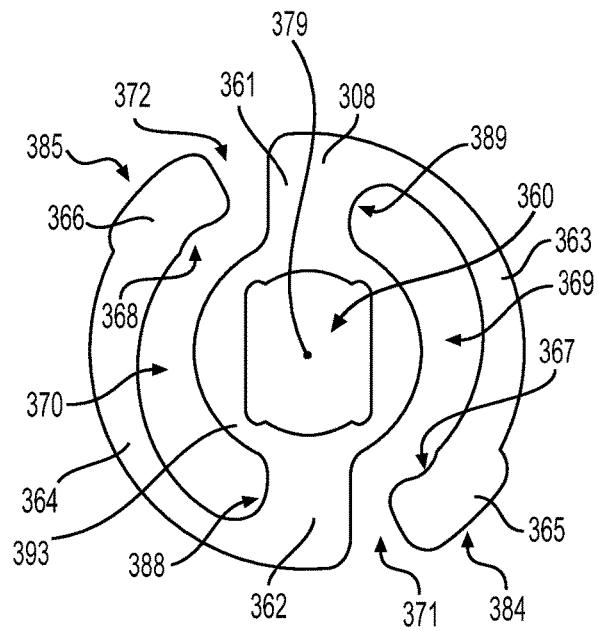
FIG. 8 illustrates a top view of an exemplary brake shoe of the braking mechanism of FIG. 3, according to aspects of this disclosure.

FIG. 8 illustrates a top view of brake shoe member 308. Brake shoe member 310 may include a central lumen 360 configured to receive central shaft 304. Central lumen 360 may be configured to receive central shaft 304 such that brake shoe member 310 is fixedly coupled to central shaft 304. A central portion 393 of brake shoe member 308 may surround central lumen 360 and may be generally circular in shape. A first protrusion 361 may extend radially outward, relative to axis 379, from central portion 393. Central axis 379 may extend through a center of central lumen 360. Note central axis 379 extends through the page in FIG. 8. A second protrusion 362 may extend radially outward, relative to axis 379, from central portion 393 and may be positioned on an opposite side of central portion 393 from first protrusion 361. Each of first protrusion 361 and second protrusion 362 may 1) have a width, measured perpendicular to axis 379, that is smaller than the width of central portion 393; and 2) have a height, measured parallel to axis 379, that is equal to the height of central portion 393.

A first arm 363 may extend outward from first protrusion 361 and may be curved towards axis 379. The width of first arm 363, measured perpendicular to central axis 379 and along a line extending through central axis 379, may increase as first arm 363 extends away from first protrusion 361. First arm 363 forms a concave curve towards or facing axis 379, and an outer surface that is also concave towards axes 379. First arm 363 may extend from first protrusion 361 to an expanded end portion 365. Expanded end portion 365 may have a curved, radially-outward facing surface 384, relative to axis 379, and surface 384 may be configured to engage wall 359 of control knob 62. Expanded end portion 365 may also include a recess 367 configured to receive one of surfaces 705, 706 of braking knob 90. Recess 367 may face radially-inward towards axis 379. A channel 369 may be formed by second protrusion 362, central portion 393, first protrusion 361, and first arm 363; and channel 369 may be configured to receive one of first protrusion 325 and second protrusion 326 of braking knob 90. Channel 369 may extend from an opening 371 between expanded portion 365 of first arm 363 and second protrusion 362 to a first end 389 at first protrusion 361.

A second arm 364 may extend outward from second protrusion 362 and may be curved towards axis 379. The width of second arm 364, measured perpendicular to central axis 379 and along a line extending through central axis 379, may increase as second arm 364 extends away from second protrusion 362. Second arm 364 has an inner surface that forms a concave curve towards or facing axis 379, and an outer surface that is also concave towards axis 379. Second arm 364 may extend from second protrusion 362 to an expanded end portion 366. Expanded end portion 366 may have a curved, radially-outward facing surface 385, relative to axis 379, and surface 385 may be configured to engage wall 359 of control knob 62. In some examples, surfaces 384, 385 may be coated by a material to increase the friction between surfaces 384, 385 and wall 359 of control knob 62. In other examples, surfaces 384, 385 may have irregular, roughened, and/or jagged surfaces, grooves, or teeth to increase friction between surfaces 384, 385 and wall 359 of control knob 62. In some examples, wall 359 may have irregular, roughened, and/or jagged surfaces, grooves, or teeth to increase friction between surfaces 384, 385 and wall 359.

Expanded end portion 366 may also include a recess 368 configured to receive one of surfaces 705, 706 of braking knob 90. Recess 368 may face radially-inward towards axis 379. A channel 370 may be formed by first protrusion 361, central portion 393, second protrusion 362, and second arm 364; and channel 370 may be configured to receive one of first protrusion 325 and second protrusion 326 of braking knob 90. Channel 370 may extend from an opening 372 between expanded portion 366 of second arm 364 and first protrusion 361 to a first end 388 at second protrusion 362.

Figure 9:
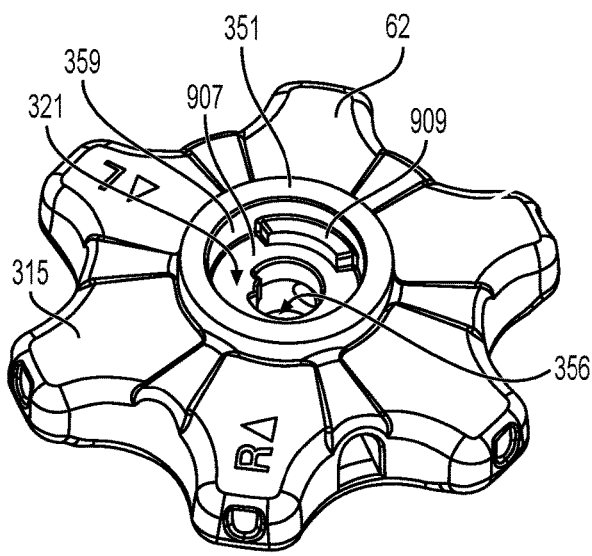
FIG. 9 illustrates a perspective view of an exemplary articulation knob of the braking mechanism of FIG. 3, according to aspects of this disclosure.

FIG. 9 illustrates a perspective view of control knob 62, and shows recess 321 configured to receive brake shoe member 308 and dual-stop member 310. Recess 321 may be formed by radially-inward facing wall 359, outward-facing surface 907, and step portion 909. Central lumen 356 extends through a central portion of control knob 62. Circular, outwardly-protruding portion 351 extends circumferentially around recess 321, and extends outward from top surface 315. Step portion 909 may be curved, may extend across outward-facing surface 907, and may be curved (concave) towards central lumen 356. Step portion 909 may be configured to engage dual-stop member 310, and may extend outward from outward-facing surface 907 a distance substantially equal to the width of dual-stop member 310.

Figure 10:
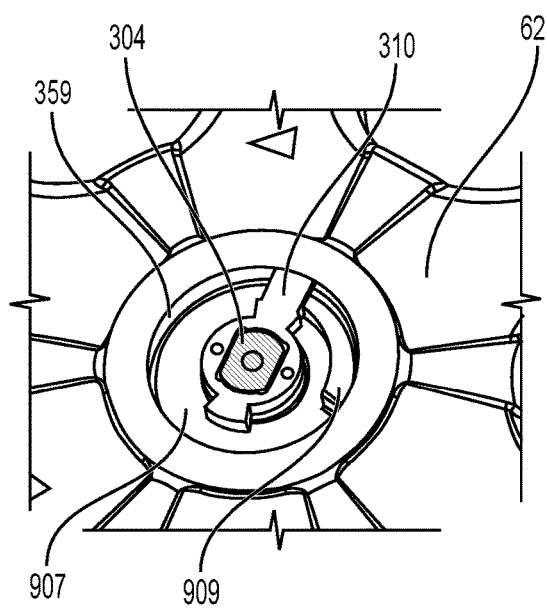
FIG. 10 illustrates a perspective view of exemplary components of the braking mechanism of FIG. 3, according to aspects of this disclosure.

FIG. 10 illustrates a perspective view of a top portion of control knob 62, dual stop member 1110 (shown in FIG. 15), and central shaft 304. Although dual stop member 1110 is shown in FIG. 10, any of the dual stop members discussed herein may be positioned in the same manner as dual stop member 1110. Central shaft 304 is shown in cross-section for clarity. Dual-stop member 1110 is shown abutting step portion 909 of control knob 62. During operation of braking mechanism 300, dual stop member 1110 may control knob 62 from rotating more than a prescribed amount via dual stop member 1110 engaging step portion 909. The dual stop 310 can be altered to allow for different rotational throw of the control knob 62, or number of degrees required to rotate dual stop 310 to apply a braking force to control knob 62. Different amounts of allowable throw may be needed based upon the connections to the drive wire system and/or tip articulation requirements at the distal end of the device. In some examples, dual stop 310 allows for approximately 260-300 degrees of rotational throw in control knob 62. Since dual stop member 310 is fixed to central shaft 304, dual stop 1110 may prevent further rotation of control knob 62 when dual-stop member 1110 contacts step portion 909 of control knob 62.

Figure 11:
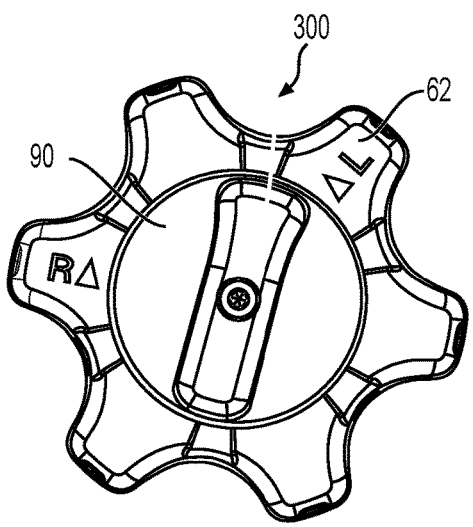
FIGS. 11 and 12 illustrate a top view and a top cross-sectional view of the braking mechanism of FIG. 3 in an unlocked position, according to aspects of this disclosure.
Figure 12:
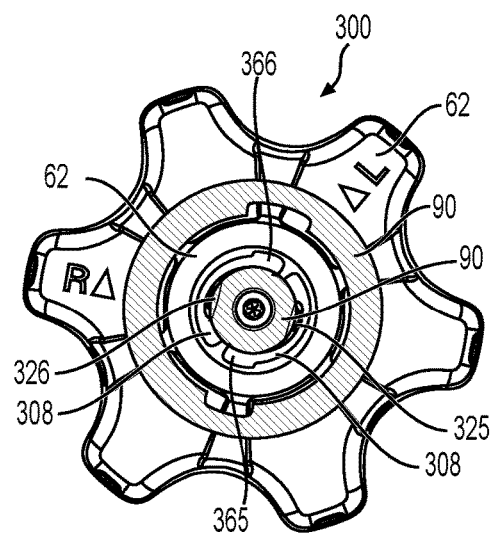

FIGS. 11 and 12 show a top view and a top, partial cross-sectional view of braking mechanism 300, respectively, in an unlocked position. Braking knob 90 is shown in cross-section in FIG. 12. When in an unlocked position, first protrusion 325 and second protrusion 326 are positioned within channels 369, 370 of brake shoe member 308 and may be positioned proximate to ends 388, 389 of channels 369, 370. In an unlocked position, expanded ends 365, 366 may be spaced from and/or not apply pressure against control knob 62 (through engagement with wall 359). In some examples, rotation of braking knob 90 in a clockwise direction may move first protrusion 325 and second protrusion 326 through channels 369, 370 and towards expanded ends 365, 366. As first protrusion 325 and second protrusion 326 move through channels 369, 370 in clockwise direction, each of arms 363, 364 may move radially-outward from axis 379 towards wall 359 due to the engagement of first protrusion 325 and second protrusion 326 with arms 363, 364. In some examples, this gradual increase in pressure applied from brake shoe member 308 to control knob 62 may provide varying degrees of braking to control knob 62, which may facilitate control of steerable device.

Figure 13:
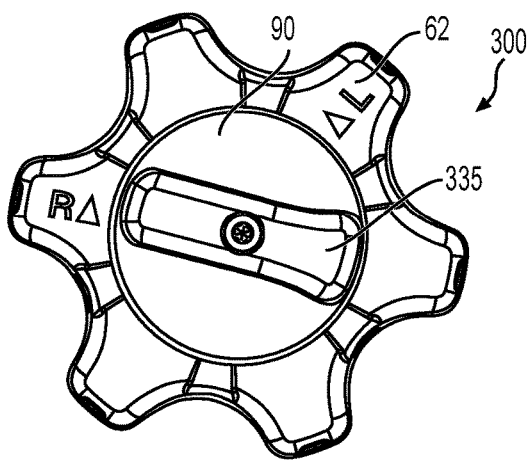
FIGS. 13 and 14 illustrate a top view and a top cross-sectional view of the braking mechanism of FIG. 3 in a locked position, according to aspects of this disclosure.
Figure 14:
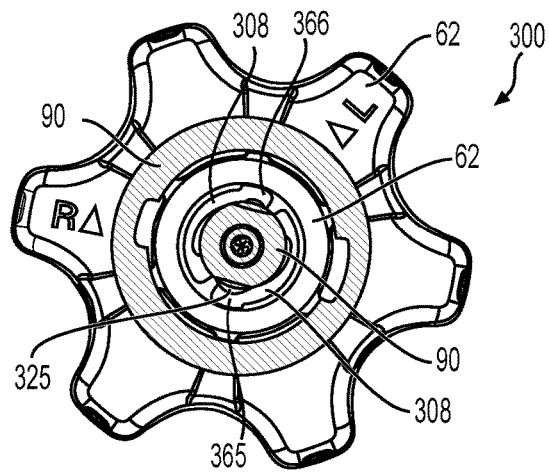

FIGS. 13 and 14 show a top view and a top, partial cross-sectional view of braking mechanism 300, respectively, in a locked position. When a user has rotated braking knob 90 to a fully locked positioned shown, first protrusion 325 and second protrusion 326 may be positioned within recesses 367, 368 of brake shoe member 308. In some examples, recesses 367, 368 may facilitate holding braking knob 90 in a fully locked position, and when a user first positions first protrusion 325 and second protrusion 326 in recesses 367, 368 an audible "click" sound my occur. In some examples, positioning first protrusion 325 and second protrusion 326 in recesses 367, 368 may provide the user with tactile feedback signifying the braking mechanism 300 is in a fully locked position. Dual-stop member 310, via its engagement with braking knob 90, may prevent the user from over-rotating braking knob 90. When first protrusion 325 and second protrusion 326 are positioned in recesses 367, 368, a user may release braking knob 62 without releasing the brake applied to control knob 62, which may facilitate operation of the steerable device and ease user fatigue from maintaining pressure on braking knob 90 to control braking.

Figure 15:
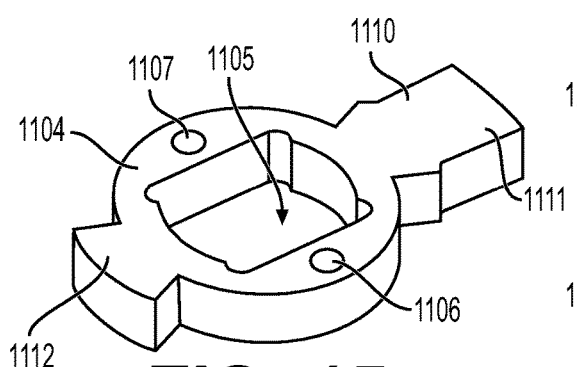
FIG. 15 illustrates a perspective view of an exemplary dual-stop component, according to aspects of this disclosure.

FIG. 15 illustrates a perspective view of an alternative embodiment of a dual-stop member 1110. Dual stop member 1110 may include any of the features discussed herein in relation to dual stop member 310. Dual stop member 1110 includes a central portion 1104, a first protruding portion 1111, a central lumen 1105, and a second protruding portion 1112. Second lumen 1106 and third lumen 1107 may be positioned at opposing portions of central portion 1104 and on opposite sides of central lumen 1105. Second lumen 1106 and third lumen 1107 may be configured to receive pins 1290, 1291 of the brake shoe member 1208 shown in FIG. 16. Dual stop member 1110 may be incorporated into braking mechanism 300.

Figure 16:
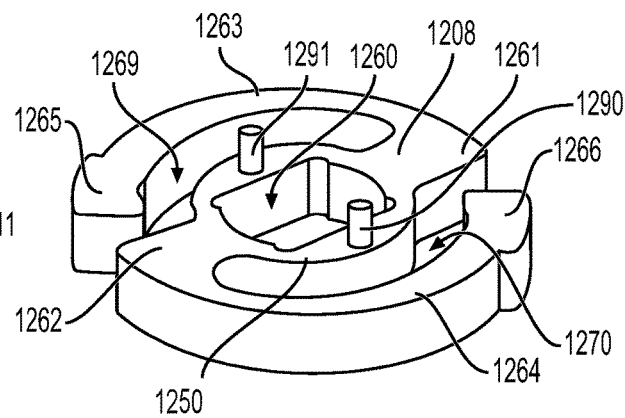
FIG. 16 illustrates a perspective view of an exemplary brake shoe, according to aspects of this disclosure.

FIG. 16 illustrates a perspective view of an alternative embodiment of brake shoe member 1208. Brake shoe member 1208 may include central lumen 1260, central portion 1250, protrusions 1261, 1262, channels 1269, 1270, and arms 1263, 1264 with expanded ends 1265, 1266. Any of the features of brake shoe member 308 may be included in brake shoe member 1208. Pins 1290, 1291 may extend outward from central portion 1250 and may be configured to be received by second lumen 1106 and third lumen 1107 of dual-stop member 1110. Pins 1290, 1291 may increase the structural integrity of brake shoe member 1208 when used in braking mechanism 300.

Figures 17, 18:
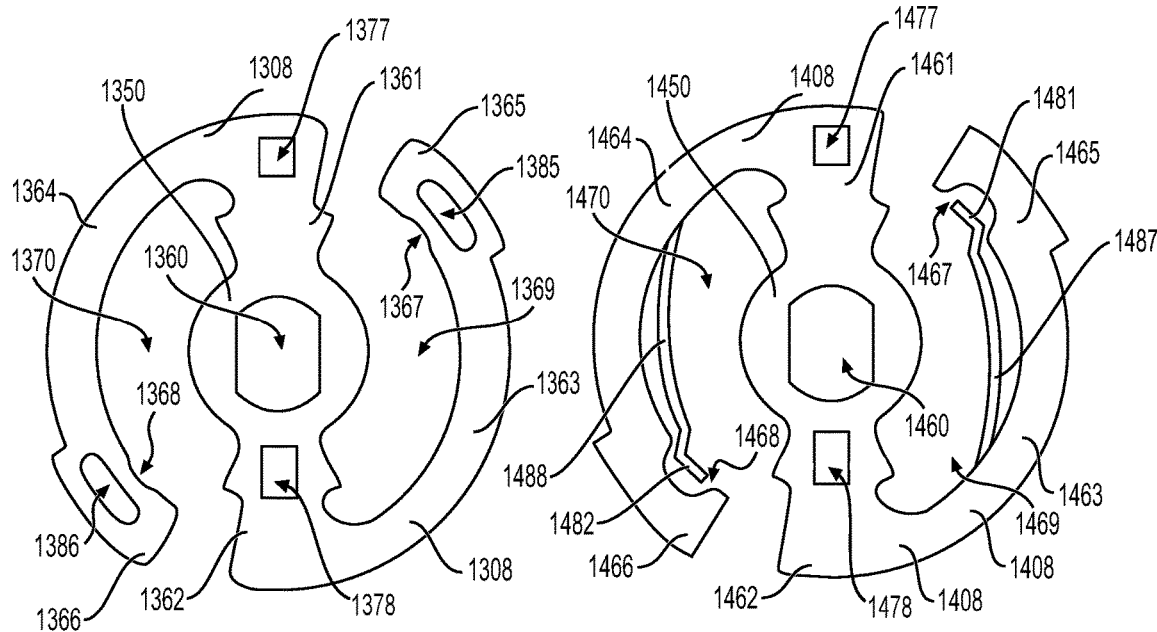
FIG. 17-20 illustrates perspective views of alternative embodiments of brake shoes, according to aspects of this disclosure.

FIG. 17 illustrates a top view of another alternative embodiment of brake shoe member 1308. Brake shoe member 1308 may include central lumen 1360, central portion 1350, protrusions 1361, 1362, channels 1369, 1370, and arms 1363, 1364 with expanded ends 1365, 1366. Any of the features of brake shoe members 308, 1208 may be included in brake shoe member 1308. Expanded ends 1365, 1366 may each include a lumen 1385, 1386, respectively, extending through a central portion of the expanded end 1365, 1366. Lumens 1385, 1386 may be positioned underneath recesses 1367, 1368 and may increase compliance of brake shoe member 1308. In some examples, brake shoe member 1308 may not include recesses 1367, 1368. When brake shoe member 1308 is used in braking mechanism 300, lumens 1385, 1386 may decrease the amount of force required to position the braking mechanism in a fully locked position. In some examples, boxed cutouts or lumens 1377, 1378, 1477, 1478, 1577, 1578 may be included in the brake shoe 1308, 1408, 1508, and each lumen 1377, 1378, 1477, 1478, 1577, 1578 may be square shaped, circular, oval, polygonal, or any other shape. In some examples, each lumen 1377, 1378, 1477, 1478, 1577, 1578 may be a recess, and not extend entirely through brake shoe 1308, 1408, 1508, instead of a lumen that extends entirely through brake shoe 1308, 1408, 1508. Each lumen 1377, 1378, 1477, 1478, 1577, 1578 may be configured to receive bent tabs or other protrusions of a dual stop, such as tabs 603, 605 of dual stop 310. Tabs 603, 605 may be pressed into each lumen 1377, 1378, 1477, 1478, 1577, 1578 to provide additional reinforcement in the braking assembly. The intent with the lumens 1377, 1378, 1477, 1478, 1577, 1578 is to allow for reinforcement of the brake shoe 1308, 1408, 1508, 1608 such that its rotationally coupled to the center shaft 304. This reinforcement may facilitate the prevention of failure in the brake shoe, dual stop, or other components, such as where a plastic, molded brake shoe can deform and slip on the center shaft 304 without the additional reinforcement of the dual stop 310. One or more lumens 1377, 1378, 1477, 1478, 1577, 1578 may be incorporated into any of the brake shoe embodiments disclosed herein.

FIG. 18 illustrates a top view of another alternative embodiment of brake shoe member 1408. Brake shoe member 1408 may include central lumen 1460, central portion 1450, protrusions 1461, 1462, channels 1469, 1470, and arms 1463, 1464 with expanded ends 1465, 1466. Any of the features of brake shoe members 308, 1208, 1308 may be included in brake shoe member 1408. Spring beams 1487, 1488 may extend through each channel 1469, 1470, respectively, and extend partially within recesses 1467, 1468, respectively. Each spring beam 1487, 1488 may include an angled end portion 1481, 1482, respectively, which may extend within each recess 1467, 1468, respectively. Spring beams 1487, 1488 may increase tactile feedback to a user when locking and unlocking braking mechanism 300, and may reduce the force required to transition braking mechanism 300 from a fully locked position to an unlocked position. Each spring beam 1487, 1488 may be spring biased towards a position away from each arm 1463, 1464, respectively. To transition from an unlocked position to a locked position, protrusions 325, 326 ride along spring beams 1487, 1488 until the protrusions 325, 326 hit end portions 1481, 1482 to force end portions 1481, 1482 into recesses 1467, 1468. Spring beams 1487, 1488 may be nylon, glass-fiber/mineral reinforced nylon, acrylonitrile butadiene styrene (ABS), polybutylene terephthalate polymer material (PBT), other injection moldable plastics, or other materials known in the art.

Figures 19, 20:
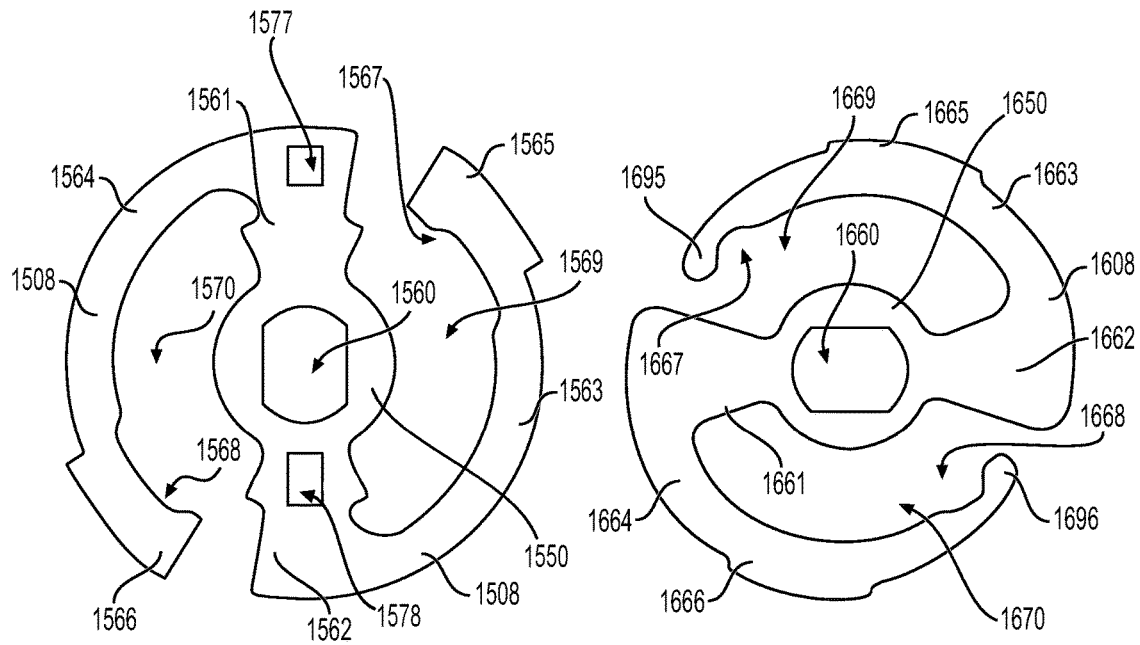

FIG. 19 illustrates a top view of another alternative embodiment of brake shoe member 1508. Brake shoe member 1508 may include central lumen 1560, central portion 1550, protrusions 1561, 1562, channels 1569, 1570, and arms 1563, 1564 with expanded ends 1565, 1566. Any of the features of brake shoe members 308, 1208, 1308, 1408 may be included in brake shoe member 1508. Each recess 1567, 1568 of arms 1563, 1564 may be expanded and may extend from a portion of each expanded end 1565, 1566 to a portion of each arm 1563, 1564 spaced from each expanded end 1565, 1566, respectively. By expanding recesses 1567, 1568, a user may adjust the amount of pressure applied by brake shoe member 1508 to control knob 62 while each of first protrusion 325 and second protrusion 326 is positioned within each recess 1567, 1568, respectively. Brake shoe 1508 may allow a user to release braking knob 90 when first protrusion 325 and second protrusion 326 are positioned within each recess 1567, 1568 without braking mechanism transitioning from a locked position to an unlocked position, and also allow a user to adjust the amount of braking power applied by braking mechanism 300 while first protrusion 325 and second protrusion 326 are positioned within each recess 1567, 1568.

FIG. 20 illustrates a top view of another alternative embodiment of brake shoe member 1608. Brake shoe member 1608 may include central lumen 1660, central portion 1650, protrusions 1661, 1662, channels 1669, 1670, and arms 1663, 1664. Any of the features of brake shoe members 308, 1208, 1308, 1408, 1508 may be included in brake shoe member 1408. Each arm 1663, 1664 may include an expanded central portion 1665, 1666, respectively. Expanded central portion 1665 may be positioned between protrusion 1662 and end 1695 of arm 1663, and expanded central portion 1666 may be positioned between protrusion 1661 and end 1696 of arm 1664. Each recess 1667, 1668 of arms 1663, 1664 may be positioned proximate to each end 1695, 1696, respectively, and may be spaced from each expanded central portion 1665, 1666, respectively. Each expanded central portion 1665, 1666 may be configured to engage wall 359 of control knob 62 to brake control knob 62. By positioning expanded central portions 1665, 1666 spaced from recesses 1667, 1668, each arm 1663, 1664 may bend or flex when braking mechanism 300 is in a fully locked position with first protrusion 325 and second protrusion 326 positioned within each recess 1667, 1668. In some examples, each arm 1663, 1664 may apply a spring force to braking knob 90 when first protrusion 325 and second protrusion 326 are positioned within each recess 1667, 1668. Although expanded central portions 1665, 1666 are shown at a central portion of each arm 1663, 1664, other embodiments may include expanded portions at any area of each arm 1663, 1664.

It also should be understood that any of the medical devices described herein may be used in medical procedures, such as for Endoscopic Submucosal Dissection (ESD), cancer treatment, kidney or bladder biopsies or resections, other procedures where removal, resection, dissection, fulguration, and/or ablation of tissue is needed, or any other therapeutic or diagnostic procedure.

Various aspects discussed herein may help reduce procedure time, increase tissue treatment effectiveness, reduce the risks to the subject, etc. Various systems and devices discussed herein may facilitate manipulation of a steerable catheter device, such as an endoscope, and may reduce user fatigue during operation.

Although the exemplary embodiments described above have been disclosed in connection with steerable catheter medical devices, a person skilled in the art will understand that the principles set out above can be applied to any medical device or medical method and can be implemented in different ways without departing from the scope of the disclosure as defined by the claims. In particular, constructional details, including manufacturing techniques and materials, are well within the understanding of those of skill in the art and have not been set out in any detail here. These and other modifications and variations are well within the scope of this disclosure and can be envisioned and implemented by those of skill in the art.

Moreover, while specific exemplary embodiments may have been illustrated and described collectively herein, it should be appreciated that any subsequent arrangement designed to achieve the same or similar purpose may be substituted for the specific embodiments described and shown herein. This disclosure is intended to cover any and all subsequent adaptations or variations of various embodiments. Combinations of the above embodiments, and other embodiments not specifically described herein, will be apparent to those of skill in the art upon reviewing the description.

While principles of the disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

Other exemplary embodiments of this disclosure will be apparent to those skilled in the art from consideration of the specification and practice of the exemplary embodiments disclosed herein. It is intended that the specification and examples be considered as exemplary only, and departures in form and detail may be made without departing from the scope and spirit of this disclosure as defined by the following claims.

We claim:

1. A steering system for a medical device, the steering system comprising:
    a brake shoe member comprising:
        a central portion including a lumen configured to receive a shaft of the medical device;
        a first protrusion extending radially-outward, relative to a central longitudinal axis of the lumen, from the central portion;
        a second protrusion extending radially-outward, relative to the central longitudinal axis of the lumen, from the central portion;
        a first arm extending outward from the first protrusion, wherein the first arm is curved and includes a first expanded end and a first recess;
        a second arm extending outward from the second protrusion, wherein the second arm is curved and includes a second expanded end and a second recess;
        a first spring beam extending from the first arm and extending at least partially within the first recess; and
        a second spring beam extending from the second arm and extending at least partially within the second recess.

2. The steering system of claim 1, wherein the first arm of the brake shoe member is configured to engage a wall of a control knob of the steering system when a braking knob is rotated in a first direction; and
    wherein the first arm is configured to move away from the wall of the control knob when the braking knob is rotated in a second direction opposite the first direction.

3. The steering system of claim 2, further comprising a dual-stop member abutting the brake shoe member.

4. The steering system of claim 3, wherein the dual-stop member is configured to limit rotation of the control knob and the braking knob.

5. The steering system of claim 3, wherein the dual-stop member is coupled to the brake shoe member via at least one pin.

6. The steering system of claim 1, wherein a first channel extends between the central portion and the first arm, wherein the first channel is configured to receive a protrusion of a braking knob of the steering system, and wherein the braking knob is configured to engage the brake shoe member to move the first arm radially outward, relative to the central longitudinal axis, towards a wall of a control knob when the braking knob is rotated in a first direction.

7. The steering system of claim 1, further comprising a control knob including a recess configured to receive the brake shoe member.

8. The steering system of claim 7, further comprising a braking knob including a first protrusion configured to abut the first arm.

9. The steering system of claim 8, wherein the braking knob includes a second protrusion configured to abut the second arm.

10. The steering system of claim 1, wherein the first expanded end includes a rough surface, grooves, and/or teeth configured to engage a wall of the medical device; and the second expanded end includes a rough surface, grooves, and/or teeth configured to engage the wall.

11. The steering system of claim 1, wherein the brake shoe member further includes:
    a first lumen extending through the first expanded end; and
    a second lumen extending through the second expanded end.

12. The steering system of claim 1, wherein the first recess extends from the first expanded end to a portion of the first arm spaced from the expanded end.

13. A steering system for a medical device, the steering system comprising:
    a brake shoe member comprising:
        a central portion including a lumen configured to receive a shaft of the medical device;
        a first protrusion extending radially-outward, relative to a central longitudinal axis of the lumen, from the central portion;
        a second protrusion extending radially-outward, relative to the central longitudinal axis of the lumen, from the central portion;
        a first arm extending outward from the first protrusion, wherein the first arm is curved and includes a first expanded end and a first recess;
        a second arm extending outward from the second protrusion, wherein the second arm is curved and includes a second expanded end and a second recess;

a first lumen extending through the first expanded end; and a second lumen extending through the second expanded end.

14. The steering system of claim 13, wherein the first arm of the brake shoe member is configured to engage a wall of a control knob of the steering system when a braking knob is rotated in a first direction; and wherein the first arm is configured to move away from the wall of the control knob when the braking knob is rotated in a second direction opposite the first direction.

15. The steering system of claim 13, further comprising a dual-stop member abutting the brake shoe member.

16. The steering system of claim 15, wherein the dual-stop member is configured to limit rotation of the control knob and the braking knob.

17. The steering system of claim 15, wherein the dual-stop member is coupled to the brake shoe member via at least one pin.

18. The steering system of claim 13, wherein a first channel extends between the central portion and the first arm, wherein the first channel is configured to receive a protrusion of a braking knob of the steering system, and wherein the braking knob is configured to engage the brake shoe member to move the first arm radially outward, relative to the central longitudinal axis, towards a wall of a control knob when the braking knob is rotated in a first direction.

19. The steering system of claim 13, further comprising a control knob including a recess configured to receive the brake shoe member.

20. The steering system of claim 13, wherein the first expanded end includes a rough surface, grooves, and/or teeth configured to engage a wall of the medical device; and the second expanded end includes a rough surface, grooves, and/or teeth configured to engage the wall.

* * * * *